United States Patent
Andrea

Patent Number: 5,909,495
Date of Patent: Jun. 1, 1999

[54] NOISE CANCELING IMPROVEMENT TO STETHOSCOPE

[75] Inventor: Douglas Andrea, Old Brookville, N.Y.

[73] Assignee: Andrea Electronics Corporation, Melville, N.Y.

[21] Appl. No.: 08/963,164

[22] Filed: Nov. 3, 1997

Related U.S. Application Data

[60] Provisional application No. 60/030,161, Nov. 5, 1996.

[51] Int. Cl.$^6$ .................................................... A61B 7/04
[52] U.S. Cl. .............................. 381/67; 181/131; 381/357
[58] Field of Search ............................... 381/67, 356, 357, 381/358; 181/131; 600/559

[56] References Cited

U.S. PATENT DOCUMENTS

| | | | |
|---|---|---|---|
| 3,314,499 | 4/1967 | Blackman | 181/131 |
| 5,492,129 | 2/1996 | Greenberger | 381/67 |
| 5,812,678 | 9/1998 | Scalise et al. | 381/67 |

*Primary Examiner*—Ping Lee
*Attorney, Agent, or Firm*—Frommer Lawrence & Haug LLP; Thomas J. Kowalski

[57] ABSTRACT

A stethoscope for reducing background noise comprising a housing having a receiver portion and an audio output means; the receiver portion having a plurality of noise ports; a microphone isolator located within the receiver portion; a noise canceling microphone having a front end and a back end enclosed by the microphone isolator; an acoustical tube having an acoustical waveguide connected to the microphone isolator for channeling an input signal; a chest piece having a sound diaphragm pickup for receiving the input sound and noise signal connected to acoustic tube to permit a pressure gradient noise porting placed at the back end of the microphone and internally behind the noise port.

2 Claims, 4 Drawing Sheets

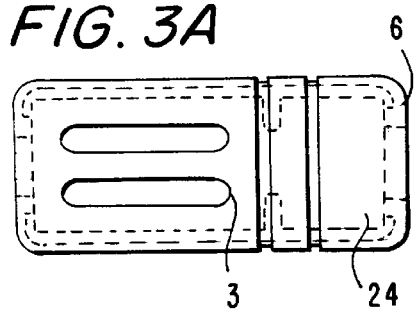
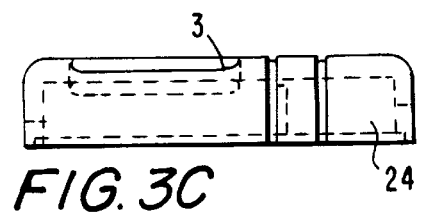
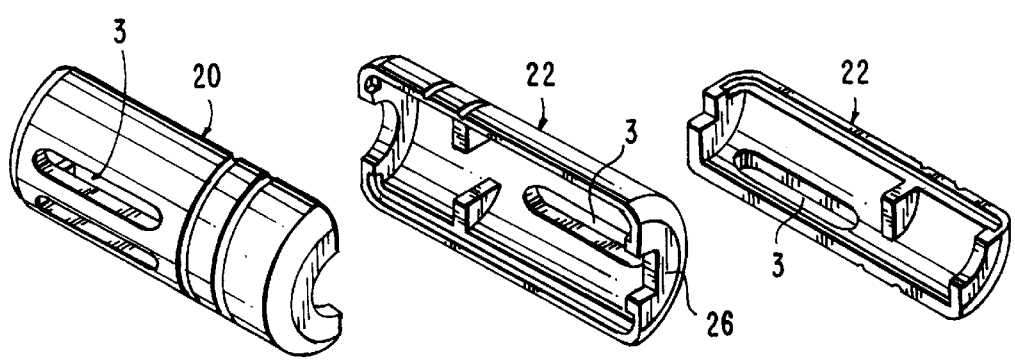

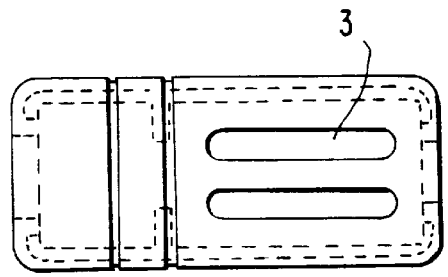 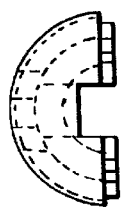
FIG. 4A  FIG. 4B
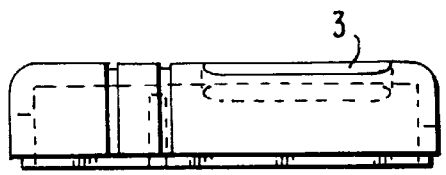
FIG. 4C
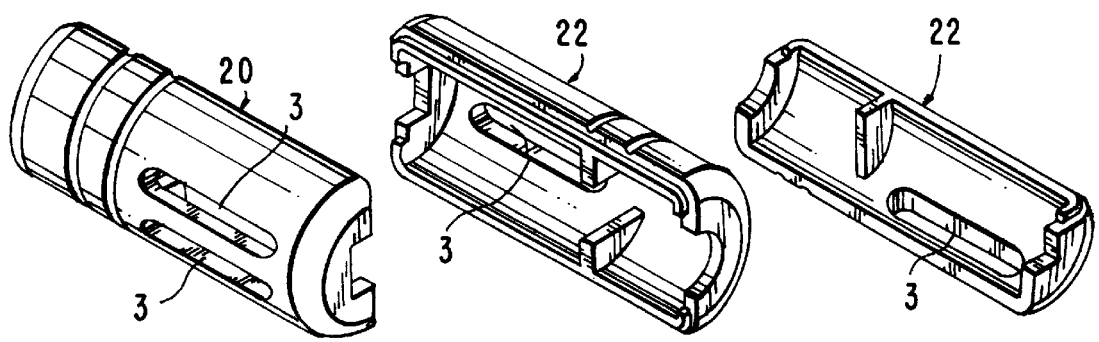
FIG. 4D  FIG. 4E  FIG. 4F

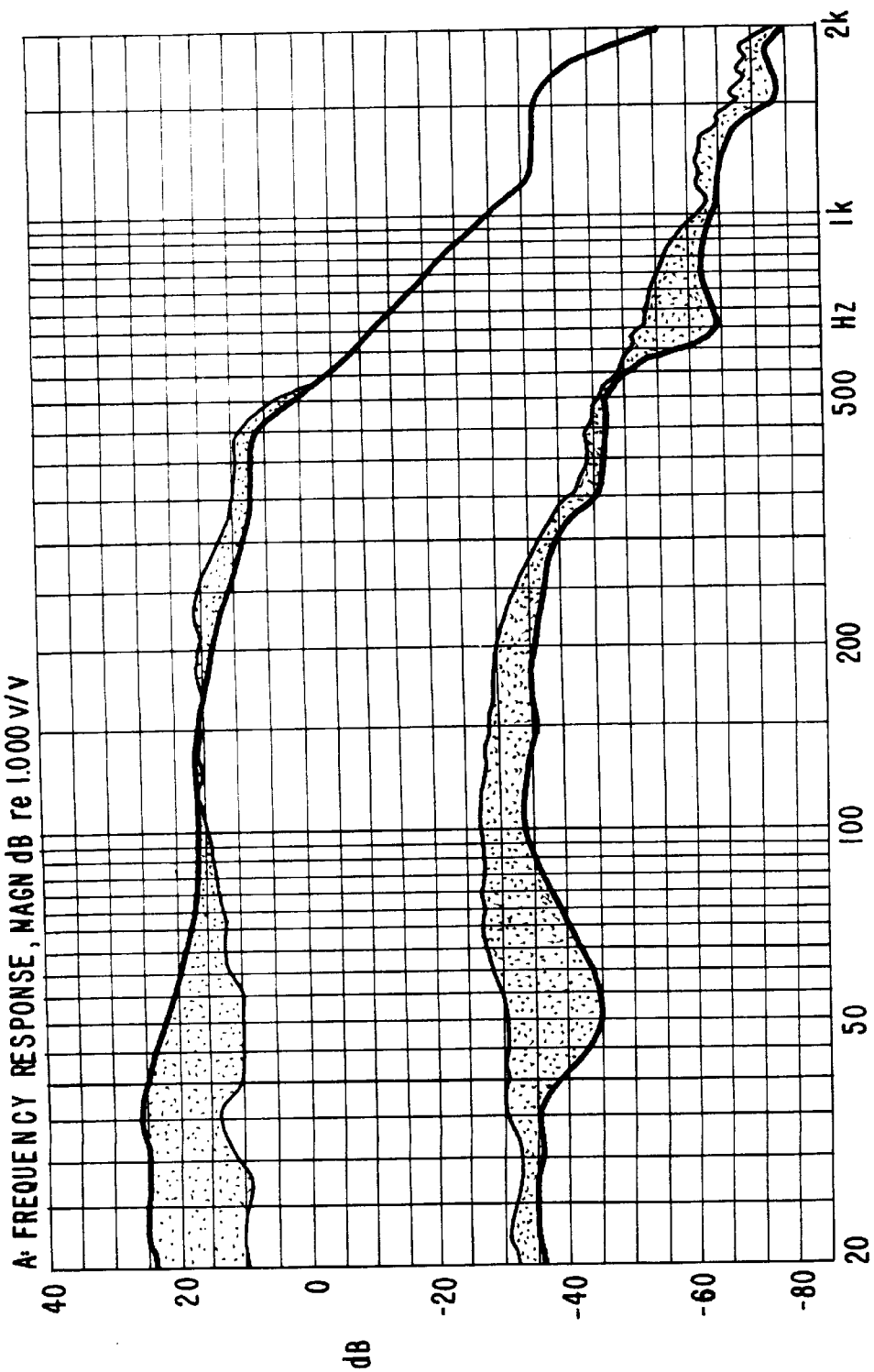

NOISE CANCELING IMPROVEMENT TO STETHOSCOPE

This application claims the benefit of U.S. Provisional Appln. No. 60/030,161 filed Nov. 5, 1996.

FIELD OF THE INVENTION

This invention relates to a noise canceling stethoscope, and, more particularly, to a pressure gradient microphone located within a microphone isolator acoustic coupler of a stethoscope for canceling or reducing background noise for listening to heart sounds of a patient located in a noisy environment.

BACKGROUND OF THE INVENTION

As is to be appreciated, in numerous situations, the presence of background acoustic noise is undesirable for a physician attempting to listen to a heartbeat or systolic murmur from a rapid heart beat of a patient to make an immediate determination or diagnosis of the patient's condition. As an example, consider the situation in which a doctor or paramedic is trying to listen with the use of a stethoscope to a heart rate of a sick person to determine the heart condition of the individual in an ambulance with a siren blaring.

In this situation, loud acoustic background noise from the siren or from any other ambient noise in the vicinity is received in a standard microphone, usually a omnidirectional microphone, located in the stethoscope housing. The noise and the sound signal are then converted to an electrical signal by the circuitry contained within the housing of a standard stethoscope. The electrical signal is then amplified and supplied to the ear of the attendant checking out the condition of the patient and is converted thereat to an acoustic signal. This resulting signal is a distorted reading of the patient's heart rate as background noise is include in the sound conveyed to a physician's ear or to a computer recording the sound of the heart rate.

As a result, the physician fails to obtain an accurate reading of the patient's heart rate because of the transmission of background noise, when utilizing a conventional stethoscope in an ambulance or noisy emergency room. Even more critical a situation is when a person has suffered a heart attack and a correct reading of the heart attack patient's heart rate could mean life or death in the next step to save the person's life. Moreover, the sound of the heart combined with the background noise may make it difficult for the doctor or nurse to monitor the heart rate to determine whether shock treatment is necessary.

Conventional or state-of-the art stethoscopes, such as the Analyst available from Heartsounds in Ontario, Canada, do not reduce or cancel background noise to improve performance of stethoscope utilized in a noisy environment or the like. Rather, the standard microphone utilized in such conventional stethoscopes are omnidirectional microphones. These standard microphones accept background and sound signals and convey an electrical signal, which is degraded by ambient noise to the electrical processing means within the stethoscope. Furthermore, an omnidirectional microphone accepts signals in all directions, including ambient noise propagating in more than one direction which is transmitted as an input signal to the microphone together with the sounds obtained from listening to the heart.

Thus, the utilization of the omnidirectional microphone in the standard stethoscope does not prevent heart sounds, especially at low frequencies, from being distorted in a noisy environment or when utilizing digital means to convey sound signal when using stethoscope. Support that the heart rate sounds are distort when using omnidirectional microphones in stethoscopes is shown in the comparative testing performed by Andrea Electronics Corporation of an Analyst stethoscope and a stethoscope made in accordance with the present invention.

For instance, the Analyst stethoscope at low frequencies that are under 1 kHz detects or picks up unwanted background noise when processing the digital heart rate received from the patient in a noisy environment, which in turns degrades the heart rate calculation. Furthermore, the Analyst is used in connection with computer software that samples the heart rate at low frequencies or at narrower bandwidths. Therefore, it is desirable to cancel noise before it is transmitted to the software sampling to prevent an inaccurate software heart rate sampling.

Conventional omnidirectional microphones located in prior art stethoscopes cannot simply be replaced with noise canceling microphones having pressure sensitive surfaces with a low gain to enhance noise canceling without typically having to reconfigure the entire stethoscope. Simple replacement of the type of microphone does not solve the problem. Rather, as will be discussed in the present invention, the mechanical/acoustical arrangement of the microphone within the necessary input ports of the microphone isolator acoustic coupler must take place so that noise cancellation occurs. This is because the mechanical/acoustical arrangement of the noise canceling microphone allows for sound equalization of the noise received from the noise port to achieve performance in calculating the number of beats per minute of the patient's heart, as such, would be relatively expensive.

Thus, the prior art has failed to provide a relatively low-cost means for reducing or canceling background noise to achieve an accurate heart rate of a patient by mechanically/acoustically diffraction means, and a cost-effective means for enabling existing stethoscope that does or does not use digital network to sample heart rates by computer means or manually by listening and recording the rate on the patient's chart.

OBJECTS AND SUMMARY OF THE INVENTION

An object of the present invention is to provide an acoustical improvement to a stethoscope which addresses the problems associated with the prior art.

Specifically, it is an object of the present invention to provide a noise canceling electronic stethoscope which reduces background noise by mechanical/acoustical means thereby permitting a physician to obtain an accurate heart rate of a patient in a noisy environment.

More specifically, it is object of the present invention to provide a noise canceling electronic stethoscope as aforementioned which is relatively inexpensive.

It is still an object of the present invention to provide a relatively low-cost noise canceling acoustical improvement to existing stethoscopes to enhance achieving a true and accurate reading of the number of beats per minute of a patient's heart to make an immediate and correct diagnosis.

Another object of the present invention is to provide an acoustical improvement to the manufacture of stethoscope or to be readily adaptable to existing stethoscope to provide a functioning noise canceling microphone that equalizes the noise received from the noise port with the noise received from the sound port to convey only the audio signal to the receiver portion having an acoustic wave guide.

An aspect of this invention is to provide a stethoscope having a noise canceling microphone placed within a noise canceling microphone pickup housing, having a microphone isolator acoustic coupler that contains a pressure gradient noise porting sized/tuned for desired frequency response, an acoustic tube having an acoustic wave guide connected to the sound diaphragm pickup of the cardiac chest piece, a microphone audio output plug, a gain trim circuit card assembly, and an acoustical opening to permit pressure gradient noise porting so that the ambient noise is mechanically canceled from the noise received with the sound received. The stethoscope for reducing background noise comprising: a housing having a receiver portion and an audio output means; the receiver portion having a plurality of noise ports; a microphone isolator located within the receiver portion; a noise canceling microphone having a front end and a back end enclosed by the microphone isolator; an acoustical tube having an acoustical waveguide connected to the microphone isolator for channeling an input signal; a chest piece having a sound diaphragm pickup for receiving the input sound and noise signal connected to acoustic tube to permit a pressure gradient noise porting placed at the back end of the microphone and internally behind the noise port. The preferred noise canceling microphone is a pressure gradient microphone.

Other objects, features and advantages according to the present invention will become apparent from the following detailed description of the illustrated embodiments when read in conjunction with the accompanying drawings in which corresponding components are identified by the same reference numerals.

BRIEF DESCRIPTION OF THE DRAWINGS

FIGS. 3A–3F are alternative perspective bottom views of the noise canceling pickup housing of the stethoscope of the present invention;

FIGS. 4A–4F are alternative perspective top views of the noise canceling pickup housing of the stethoscope of the present invention; and FIG. 5 is a frequency response curve of a noise canceling electronic stethoscope as compared with a frequency response curve of an omnidirectional microphone of a prior art stethoscope.

DETAILED DESCRIPTION

Figure 1:
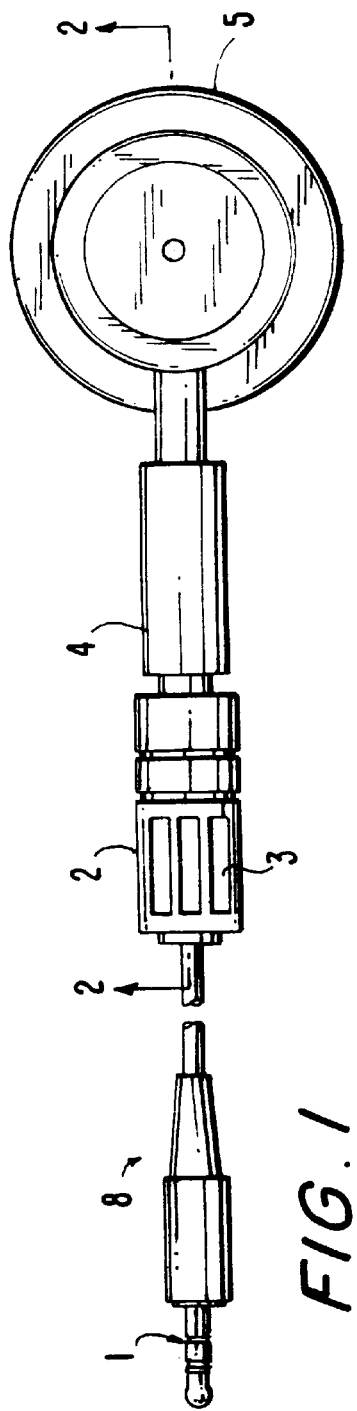
FIG. 1 is a top plan view of the stethoscope having a noise canceling acoustical/electrical improvement according to the present invention.

FIG. 1 illustrates a stethoscope 8 utilizing a noise canceling acoustical/electronic improvement in accordance with an embodiment of the present invention. As shown therein, the stethoscope 8 has a microphone audio output plug 1 located at the proximal end with the chest piece 5 at the proximal end of the stethoscope 8. The microphone audio output plug 1 is connected to the noise canceling microphone pickup housing 2, which contains a plurality of ports used for pressure gradient noise porting as seen in FIG. 1. The mechanics and dimensions of the noise canceling microphone pickup housing 2 will be discussed in FIGS. 3–4, which housing provides a close fit that allows the noise canceling microphone 7 to detect pressure changes without leakage. The pickup housing 2 is then connected to an acoustic tube 4, which comprises the acoustic wave guide 12 for funneling the identical sound and background noise signal detected by the sound diaphragm 13 picked up from the standard cardiac chest piece 5 as shown in FIG. 2.

Figure 2:
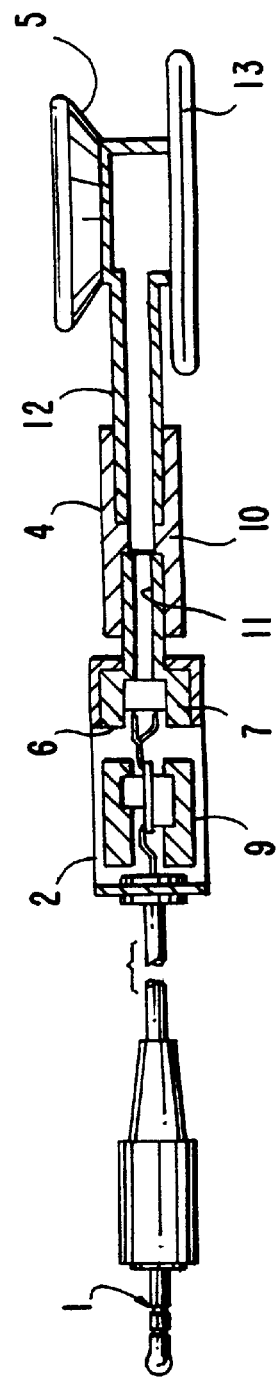
FIG. 2 is a cross-sectional view of FIG. 1 taken along A—A.

As shown in FIG. 2, the noise canceling microphone pickup housing 2 generally includes a microphone isolator acoustic coupler 6, a plurality of noise ports 3, an audio output plug 1, a noise canceling microphone 7, and dense foam 10. The acoustic coupler 6 can be comprised of rubber, dense foam-like material, or another suitable damping material. This coupler 6 is located beneath the acoustical port holes inside the housing in close proximity to the noise canceling microphone 7. This microphone 7 of the present invention is preferably a pressure gradient microphone available from Panasonic or Primo. Alternatively, a unidirectional microphone that has a FET with a low gain having low sensitivity can be used as it is more effective for active noise cancellation. These low sensitive microphone with low gain that accept near field responses can be utilized in the present invention as the sounds received from listening to a patient's heart are in the low frequency bandwidth of less than 1 kHz or 70 Hz.

The pressure sensitive microphone 7 has a front end and a back end having pressure sensitive surfaces with holes or openings on each surface (not shown). These holes permit sound to enter from the back of this microphone as well as the front of this microphone. The pressure gradient microphone 7 responds to a difference in pressure that is detected from the sound diaphragm pickup 13 of the chest piece 5. Therefore, to have effective noise cancellation in the present invention the sound pressure of the background noise must arrive simultaneously or at approximately the same time with the sound pressure from the background noise and audio signal received from the sound diaphragm 13 that is funneled through the acoustic channel 11 of the acoustic wave guide 12 located within the acoustic tube 4.

When the pressure sensitive microphone is place in the stethoscope 8 as shown in FIG. 2, the microphone isolator acoustic coupler 6 and ports 3 must be so arranged so that the noise entering from the back of the microphone from the noise port 6 and the noise and heart sounds entering from the acoustic channel 11 of the acoustic tube 4 equalize or cancel out the noise portion of the signal is identical. The signal that is transmitted to the microphone is converted to an electrical signal and is scaled or adjusts the input signal by the gain trim circuit card assembly 9 so just sound is conveyed to the audio output plug 1.

As stated, the preferred pressure gradient microphone 7 responds to the difference in pressure at two closely spaced ports, the noise ports 3 and the sound diaphragm pickup 13. When used in an environment where the pressure gradient of the background noise is isotropic, for instance the noise in a hospital emergency room or in an ambulance, the electrical signal produced by the pressure-gradient microphone due to such background noise is effectively zero if the sound pressure remains identical. Since the two opposite sides of a pressure-gradient microphone respond to acoustic pressure, as previously mentioned, the microphone isolator 7 is created or modified so as to enable these two sides of the microphone to respond simultaneously with the acoustic pressure detected by the noise ports 3 and the sound diaphragm pickup 13, which signals are funneled through the acoustic wave guide 12.

Therefore, the ambient noise that enters from the noise ports as a result of a doctor's heavy breathing, siren blaring, or background talk reaches the pressure gradient microphone at the same pressure sensitivity as the noise and heartbeat sounds detected by the diaphragm pickup 13 of the chest piece 5 that is channeled by the acoustic channel 11 located within the acoustic wave guide 12. Thus, by acoustical/mechanical means, the pressure of the background noise are equalizes to an effective zero, which allows an accurate heart rate to be calculated by the number of beats per minute.

To achieve the optimal performance of the noise canceling microphone 7 located in the stethoscope 8, the microphone isolator acoustic coupler 6 is comprised of two members 20, 22 shown in FIGS. 3–4 together with dense foam material that are welded together by non-flux soldering. Non-flux soldering prevents future resin contamination of the noise canceling microphone 7 located at the bottom half 24 of the acoustic coupler 6. Conventional flux based soldering material would interfere with the proper functioning of a noise canceling microphone rendering it inoperative.

In FIGS. 3A–3F varying bottom views of the front and rear housing members 20, 22 are shown in FIGS. 3D–3F. FIG. 3D shows the front isometric member, FIG. 3E shows the rear isometric member, and FIG. 3F shows the section isometric member. In FIG. 3A, a top view of the assembled microphone isolator acoustic coupler 6 having noise port holes 3 is shown. The length of each of the noise ports is preferably 0.6 inches and the width of each port is preferably 0.093 inches and preferably spaced apart at 0.090 inches to achieve the desired noise cancellation curves shown in FIG. 5. The given dimensions of the acoustic coupler 6 allows for pressure gradient noise porting or noise flow through from the noise ports 3 to reach the pressure gradient microphone surface to cancel out with the noise flow combined with sound received from the chest piece 5, which provides for the desired frequency responses shown in FIG. 5.

In FIG. 3B, the bottom corner 26 of the acoustic coupler 6 is shown. The corner having a squared end to facilitate the sound pressure flow as shown in FIG. 3E.

In FIGS. 4A–4F varying top views of the front and rear housing members 20, 22 are shown in FIGS. 4D–4F. FIG. 4D shows the front isometric member, FIG. 4E shows the rear isometric member, and FIG. 4F shows the section isometric member. In FIG. 4A, a top view of the assembled microphone isolator acoustic coupler 6 having noise port holes 3 is shown. The length, width and spacing of each of the noise ports is identical to the dimensions provided In FIGS. 3A–3F. In FIG. 4B, the top corner 26 of the acoustic coupler 6 is shown having a squared end identical to FIG. 3B.

These acoustical modification permits pressure gradient noise porting so that the noise is mechanically/acoustically canceled or diffracted before transmittal to the gain trim circuit card assembly 9, where the electrical signal is scaled so that substantially heart sounds is transmitted to the microphone audio output plug 1 for digital recordation or manually recordation on a patient's chart.

The acoustic coupler 6 is sized and tuned for permitting low frequency responses of sound to be eventually conveyed to the audio output plug 1. The acoustic coupler 6 comprises an acoustic channel 11 connected to the acoustic wave guide 12 for channeling the input signal received from the cardiac chest piece 5 by the sound diaphragm pickup 13 that detects the heart sound and pickup noise from the surrounding environment. The preferred manufacturers of the cardiac chest piece 5 are Mark IV Labtron and Grafco.

The cardiac chest piece 5 contains an acoustic wave guide 12 that is located beneath the cardiac chest piece 5 and above the sound diaphragm pickup 13 shown in FIG. 2. The acoustic wave guide 12 is comprised of dense foam-like material, preferably 100 ppi plosive windscreen, inserted internally behind the cardiac chest piece 5 of the stethoscope 8 in FIG. 2. The purpose of the sound diaphragm 13 is to detect as an input signal the heart beat and wind noise, breathing sounds, or other ambient noises that exist when utilizing the stethoscope in a noisy atmosphere or outdoors. The acoustic wave guide 12 acts as a structural baffle to channel the identical input signal from the sound diaphragm pickup 13 to the noise canceling microphone 7.

The two lead wires (not shown) of the noise canceling microphone 7 were connected to the circuitry contained on the gain trim circuit card assembly 9 that consist of amplifiers, resistor coupled to a capaciatator (not shown) to scale or adjust the electrical signal before being transmitted as sound to the microphone audio output plug 1. Additional circuits (not shown) enable calibration processing to be performed on preferably a pressure gradient microphone or unidirectional microphone having a low FET gain and low sensitivity characteristics.

The circuitry wires must be oriented and preferably placed so as not to cover or adversely affect the flow of sound conveyed through the acoustical wave guide 12 and the noise ports 3 to the noise canceling microphone 7. The lead wires must not interrupt the flow of noise that is received from the ports and channel, which is eventually canceled from the audio sound signal. The procedure to install at least one noise canceling microphone 12 in a stethoscope requires a non-flux soldering.

As is to be appreciated, by using the above-described devices and materials for acoustically improving the receiver portion of the conventional stethoscope, the cost for constructing such receiver portion is relatively low. Further, the power consumption of the receiver portion is kept relatively low. As a result, the receiver portion does not require additional power or transformers or the like. Furthermore, although the receiver portion (not shown) has been described for assembly with existing stethoscope, such receiver portion, or a slight variation thereof, may be installed in new stethoscope to be manufactured, like Heartsounds' Analyst.

Upon activating the stethoscope 8, e.g., by listening to a heart beat detected from the cardiac chest piece 5 and the sound diaphragm 13, a signal from the noise canceling microphone 7 is supplied through a circuit card assembly 9, preferably for gain trimming comprising a resistor and a capacitor coupled to an operational amp and then outputted as a resulting audio signal to the output plug 1.

FIG. 5 is active noise cancellation curves showing the improved cancellation with the noise canceling acoustical embodiment of the present invention. The top line, representing near field responses and the bottom line, representing far field responses with the gray shaded area noting the cancellation occurring using a noise canceling stethoscope of the present invention. These tests were conducted at the facilities of Andrea Electronics Corporation. The shaded gray area represents the noise canceling improvement in particular from 20 Hz to 200 Hz utilizing the present invention of FIGS. 1–2. For instance, at 50 Hz, the combined improved noise cancellation was 27 dB or 15 dB of background noise canceled in the far field response and almost 12 dB canceled at near field response utilizing a stethoscope made in accordance with the present invention. The critical frequency range for listening to heart rates is approximately 70 Hz, where there is a combined noise cancellation of about 17 dB. However, at far speaking range, exceeding 1 kHz the pressure gradient microphone had no real effect. For instance, at 1 kHz, there was only about a 2 dB change with using a noise canceling microphone in a stethoscope.

Furthermore, although preferred embodiments of the present invention and modifications thereof have been described in detail herein, it is to be understood that this invention is not limited to those precise embodiments and modifications, and that other modifications and variations may be affected by one skilled in the art without departing from the spirit and scope of the invention as defined by the appended claims.

What is claimed is:

1. A stethoscope for reducing background noise comprising:
   a housing having a receiver portion and an audio output means;
   the receiver portion having a plurality of noise ports;
   a microphone isolator located within the receiver portion;
   a noise canceling microphone having a front end and a back end enclosed by the microphone isolator;
   an acoustical tube having an acoustical waveguide connected to the microphone isolator for channeling an input signal;
   a chest piece having a sound diaphragm pickup for receiving the input sound and noise signal connected to said acoustical tube to permit a pressure gradient noise porting by said noise ports placed at the back end of the microphone which is internally located before the noise ports.

2. The stethoscope of claim 1 wherein the noise canceling microphone is a pressure gradient microphone.

* * * * *